United States Patent [19]

Sumi et al.

[11] Patent Number: 5,221,738
[45] Date of Patent: Jun. 22, 1993

[54] CDNA AND GENOMIC DNA ENCODING THE AMINO ACID SEQUENCE OF HUMAN $\alpha_2$-PLASMIN INHIBITION

[75] Inventors: Yoshihiko Sumi, Hino; Yataro Ichikawa; Masami Murakami, both of Tokorozawa; Nobuo Aoki, Tokyo, all of Japan

[73] Assignee: Teijin Limited, Osaka, Japan

[21] Appl. No.: 803,896

[22] Filed: Dec. 9, 1991

Related U.S. Application Data

[63] Continuation of Ser. No. 134,301, Dec. 15, 1987, abandoned.

[30] Foreign Application Priority Data

Dec. 19, 1986 [JP] Japan ............................ 61-301753
Jun. 23, 1987 [JP] Japan ............................ 62-154495

[51] Int. Cl.$^5$ .................... C07H 21/04; C12N 15/55; C12N 9/18
[52] U.S. Cl. .................. 536/29.2; 536/23.5; 530/380
[58] Field of Search .................... 536/27–29

[56] References Cited

FOREIGN PATENT DOCUMENTS 0257630 3/1988 European Pat. Off. .

OTHER PUBLICATIONS

Holmes et al., "Primary Structure of Human $\alpha_2$-Antiplasmin, a Serine Protease Inhibitor(Serpin)," *J. Biol. Chem.*, 262(4), 1659–1664 (1987).

Sumi et al., "Structure of the Carboxyl-Terminal Half of Human $\alpha_2$-Plasmin Inhibitor Deduced from that of cDNA," *J. Biochem.*, 100, 1399–1402 (1986).

Moroi et al., "Isolation and Characterization of $\alpha_2$-Plasmin Inhibitor for Human Plasma," *J. Biol. Chem.*, 251(17), 5956–5965 (1976).

*Primary Examiner*—Johnnie R. Brown
*Assistant Examiner*—L. Eric Crane
*Attorney, Agent, or Firm*—Wenderoth, Lind & Ponack

[57] ABSTRACT cDNA encoding a human $\alpha_2$-plasmin inhibitor precursor protein represented by an amino acid sequence from the −39th Met to the 452nd Lys in FIG. 1 of the accompanying drawings; an amino acid sequence of a human $\alpha_2$-plasmin inhibitor precursor represented by an amino acid sequence from the −39th Met to the 452nd Lys in FIG. 1 of the accompanying drawings; and genomic DNA encoding a human $\alpha_2$-plasmin inhibitor protein which is composed of exons II, III, IV, V, VI, VII, VIII, IX and X in FIG. 4 of the accompanying drawings, said exons being bonded to one another via introns.

7 Claims, 11 Drawing Sheets

FIG. 1(1)

```
                                                                    GAG    3
       -39
       MetAlaLeuLeuTrpGlyLeuLeuValLeuSerTrpSerCysLeuGlnGlyProCys    -21
       AACATGGCGCTGCTCTGGGGGCTCCTGGTGCTCAGCTGTCCTGCCTGCAAGGCCCCTGC    63

-20
SerValPheSerProValSerAlaMetGluProLeuGlyArgGlnLeuThrSerGlyPro         -1
TCCGTGGGCTCCCCTGTGAGCGCCATGGAGCCCTTGGGCCGGCAGCTAACTAGCGGGCCG        123

+1                                                                   20
AsnGlnGluGlnValSerProLeuThrLeuLeuLysLeuGlyAsnGlnGluProGlyGly
AACCAGGAGCAGGTGTCCCCACTTACCCTCCTCAAGTTGGGCAACCAGGAGCCTGGTGGC        183

40
GlnThrAlaLeuLysSerProProGlyValCysSerArgAspProThrProGluGlnThr
CAGACTGCCCTGAAGAGTCCCCCAGGAGTCTGCAGCAGAGACCCCACCCCAGAGCAGACC        243

60
HisArgLeuAlaArgAlaMetMetAlaPheThrAlaAspLeuPheSerLeuValAlaGln
CACAGGCTGGCCCGGGCCATGATGGCCTTCACTGCCGACCTGTTCTCCCTGGTGGCTCAA        303

80
ThrSerThrCysProAsnLeuIleLeuSerProLeuSerValAlaAlaLeuSerHis
ACGTCCACCTGCCCCAACCTCATCCTGTCACCCCTGAGTGTGGCCCTGGCCCTGTCTCAC        363

100
LeuAlaLeuGlyAlaGlnAsnHisThrLeuGlnArgLeuGlnValLeuHisAlaGly
CTGGCACTAGGTGCTCAGAACCACACAGTTGCAGAGGCTGCAACAGGTGCTGCACGCAGGC      423
```

FIG. 1 (2)

```
                                                                                   120
SerGlyProCysLeuProHisLeuLeuSerArgLeuCysGlnAspLeuGlyProGlyAla
TCAGGGCCCTGCCTCCCCCATCTGCTGAGCCGCCTCTGCCAGGACCTGGGCCCCGGCG       483

140
PheArgLeuAlaAlaArgMetTyrLeuGlnLysGlyPheProIleLysGluAspPheLeu
TTCCGACTGGCTGCCAGGATGTACCTGCAGAAAGGATTTCCAATCAAAGAAGATTTCCTG    543

160
GluGlnSerGluGlnLeuPheGlyAlaLysProValSerLeuThrGlyLysGlnGluAsp
GAACAATCCGAACAGCTATTTGGGGCAAAGCCCGTGAGCCTGACGGGAAAGCAGGAAGAT    603

180
AspLeuAlaAsnIleAsnGlnTrpValLysGluAlaThrGluGlyLysLysIleGlnPhe
GACCTGGCAAACATCAACCAATGGGTGAAGGAGGCCACGGAGGGGAAGATTCAGGAATTC    663

200
LeuSerGlyLeuProGluAspThrValLeuLeuLeuAsnAlaIleHisPheGlnGly
CTCTCTGGGCTGCCGGAAGACACCGTGTTGCTTCTCCTCAACGCCATCCACTTCCAGGGT   723

220
PheTrpArgAsnLysPheAspProSerLeuThrGlnArgAspSerPheHisLeuAspGlu
TTCTGGAGGAACAAGTTTGACCCGAGCCTTACCCAGAGAGACTCCTTCCACCTGGACGAG   783
```

FIG. I (3)

```
            240
GlnPheThrValGluMetMetGlnAlaArgThrTyrProLeuArgTrpPheLeu
CAGTTCACGGTGCCCGTGGAAATGATGCAGGCCCGCACGTACCCGCTGCGCTGGTTCTTG    843

260
LeuGluGlnProGluIleGlnValAlaAlaHisPheProPheLysAsnAsnMetSerPheVal
CTGGAGCAGCCTGAGATCCAGGTGGCTGCTCATTTCCCCTTTAAGAACAACATGAGCTTTGTG    903

280
ValLeuValProThrHisPheGluTrpAsnValSerGlnValLeuAlaAsnLeuSerTrp
GTCCTTGTACCCACTCACTTTGAATGGAACGTGTCCCAGGTACTGGCCAACCTGAGTTGG    963

300
AspThrLeuHisProProLeuValTrpGluArgProThrLysValArgLeuProLysLeu
GACACCCTGCACCCACCCCTCGTGTGGGAGAGGCCCACCAAGGTCCGGCTCCCTAAGCTG    1023

320
TyrLeuLysHisGlnMetAspLeuValAlaAlaThrLeuSerGlnLeuGlyLeuLeu
TATCTGAAACACCAAATGGACCTGGTGGCCGCCACCCTCAGCCAGCTGGGCCTCAGGAGTTG    1083

340
PheGlnAlaProAspLeuArgGlyIleSerLeuGluGlnSerLeuValValSerGlyValGln
TTCCAGGCCCCCAGACCTGCGTGGGATCTCCGAGCAGAGCCTGGTGGTGTCCGGCGTGCAG    1143

360
HisGlnSerThrLeuGluLeuSerGluValGlyValAlaAlaAlaAlaThrSerIle
CATCAGTCCACCCTGGAGCTCAGCGAGGTCGGGGAGGTTGGGGCGGCCGCCACCAGCATT    1203
```

FIG. I (4)

```
                                                                        380
AlaMetSerArgMetSerLeuSerSerPheSerValAsnArgProPheLeuPhelle
GCCATGTCCCGCATGTCCCTGTCCCTTCAGCGTGAACCGCCCCTTCCTCTTCATC                 1263
                                                                        400
PheGluAspThrThrGlyLeuPheValGlySerValArgAsnProAsnProSer
TTCGAGGACACCACAGGCCTTCCCCTCTTCGTGGGCAGCGTGAGGAACCCCAACCCCAGT            1323
                                                                        420
AlaProArgGluLeuLysGluGlnAspSerProGlyAsnLysAspPheLeuGlnSer
GCACCGCGGGAGCTCAAGGAACAGGATTCCCGGGCAACAAGGACTTCCTCCAGAGC                1383
                                                                        440
LeuLysGlyPheProArgGlyAspLysLeuPheGlyProAspLeuLysLeuValProPro
CTGAAAGGCTTCCCCCGCGGGGAGAACAAGCTTTTCGGCCCCTGACTTAAAACTTGTGCCCCCC        1443
                   452
MetGluGluAspTyrProGlnPheGlySerProLys
ATGGAGGAGGATTACCCCCAGTTTGGCAGCCCCAAGTGAGGGGCCGTGGCTGTGGCATCC            1503

AGAGTCCCTGCCTGACCAGCCTCTCCACTCATGTGACTCTTTCCAACCTGCTTTGTGGC             1563

ACTGGGGCAGGGCCGGGGGCAGTCTGAGAGAGGCCATTCTTTCCCAACACCTCTTGGGG             1623

AGTTTAGGGTGGGGGGGGCGCTGGGAGGGCTGGGAGGAGGGCAGGCATCGGGAGCCGGGAGCCT        1683
```

FIG. I (5)

```
GACCCTCATCTTTCTTCCAAACAGGCTCAGAGGGTGTCCTGCACCGGGGCCTGGGCAGGA  1743
GGGAGGTGCTTCTAGTTCTGCCAGGAGACAGGTTAGCTGCTCCCCACGTCAGCTGGGACA  1803
CCCCGACTTTTGTTTACCAGAGAAAAAGGGAGGGGAGAGGGCTGCCTTTGGACTTGTCC   1863
CGGGACACCTAGGCTAGGGTGGGGAGAGACGGGCCCTGGTGGCTCGGGAGGCGAAGC     1923
GTTGTCCTCAGCCCCGTGGAACTCGTGTCTGGCACAGCCTGGCTGTGGCCTAACCTGC    1983
CGAGAGTCCATCAGCCTCCATCCTACCCCCTGCCTTGTCACCCCAGACTTCCCACGGC    2043
TCCTCGAGATCCCAACACTGCCAGCATTTCCCTTCCTTCCTCCTGTCTCCCTCCTCTG    2103
CCCGGGAGCTCAGGAACCGAGGCAGGGAAGGATCCCATGAGCTCCTTAAGGCTCTTTTGT  2163
AAGGTTTTGTAGTGATTTTTATGCCACCTGAATAAAGAATGAATGGGCAAAAAAAAAA    2223
AAAAAAAAAAAAAAAAAAAAAAAAA                                     2249
```

FIG. 4 (I)

```
                                                                                              ⎫
-270    -260    -250    -240    -230    -220    -210    -200    -190                          |
CCC AGC CAT CAG CCC CAG TGG CCT AGT GTC CCG GCT TCA TGT GCT CCT GGA CAC CCG CAC GGG CCC TTC TGC GAG CTG |
    -180    -170    -160    -150    -140    -130    -120    -110    -100    -90              |
GCC AGC CAC GAG GGC AGT TCT GCA GGT CAA GGT CCG CTT CCT CCC CTT GCT GCC CAA CCG CTG TCC ACC CAT CAC CCC |  EXON I
    -80    -70    -60    -50    -40    -30    -20    -10                                      |
TGC TTA GGG TCT GCC TCC CCG GGT TCA GCC TCG AAC TGG TCT GTC TTA TAT ACC TGG TCC AGG GCA GGG AGG TAG CCT CTC GGT CCA |
                                                                                              |
CCT TGG GAG CCA GTT GCA CTG CAG................intron 1 (~8 kb).........                      ⎭

........AAA AAT CCC AAA AGA CGG

TCT TAT TTG GTC CTC ACC ATG CAT GTG AGA AGA GTG AGG GAC TTT GTG CCA TTT TAC AAG GTA GTG GAG CTG TTA CGG ATG
CCA GGA TTG GCA AGA GGT AGC CTG GAT TCA GAC ACA GAT CTG AGC ATT CAC AGC CTG TGT AGA ATG AGA ACG TTT TTG ATT TGG TAT CTC
CCT CCT ATT CAC CAA AAC ACC TTC CGA TGA ATT GCA TGA AAT ATG AAA CTA AAA AGG GGA AGA ACC CTG GCC GGA TGT CCC AGC
TGC AGT AGT GGG AGC GCC TCC TGG TGT TGT TGA GCC CTT CTT CCC TTG GCA ATC ATG ACC CCA GGA CTT GCC GTT        ⎫
                                                                                             -1 +1      |
ATC TGT GAT CGC GTG GGT AGG ATT CCT GCC CGT GGG CCC GAT GTG CAG ACA GAG CTT TCT GTC CCT GCC CAC AGG AAC ATG GCG  EXON II
                                                                                       Met Ala         |
TGG GGC CTG GTC CTG GTC CTC AGC TGG CTC GTG GTC TCC CTG CAA GGC CCC TCC CTG GTG AGC GCC ATG GAG CCC TTG GCC CGG |
Trp Gly Leu Val Leu Val Leu Ser Trp Cys Leu Gln Gly Pro Ser Val                        Met Glu Pro Leu Gly Arg |
 20          30           40          50          60           -20                                             |
                                                                                        intron 2              ⎭
CTT GCC ATG AGG AGG AGT GAG GGG AGT GAG CCT GTG ATG GGG GGA AGG TCC CGG GAC CTT ACC CTA TCC CTT CTT CCA CAG TTC TCC CCT GTG AGC GCC ATG GAG CCC TTG GCC CGG
                                                                                        Phe Ser Pro Val Ser Ala Met Glu Pro Leu Gly Arg
                                                                                         70       80           90                -10
                                                                                                                                     ⎫
                                                                                                                                     | EXON III
                                intron 3                                                                                             ⎭
                                                                                                                                     ⎫
CAG GTA CTG GGG AGT GAG GAG GAG CCT GTG ATG GGG GGA AGG TCC CGG GAC CTT ACC CTA TCC CTT CTT CCA CAG TCT CAC TGG CCT TGG GCA GGG TCC CCA CTT ACC CTC AAG TTG GCC CTT ACC CTC AAG TTG GCC ACC CTT GGG AAG GGT CGG  EXON IV
 100                                                                                                                                 |
CAG                                                                                                                                  |
Gln                                                                                                                                  |
                                                                                                                                     |
TCT CCA TCT GCT TCC TCC TTT CCG CAG CTA ACT AGC GGG GAG CCG AAC CAG GAG CAG GTG TCT CAC TGG CCT TGG GCA GGG TCC CCA CTT ACC CTC AAG TTG GCC AAC CAG GTA CAA
Leu Thr Ser Gly Pro Asn Gln Glu Gln Val Ser Pro Leu Thr Leu Lys Leu Gly Asn Gln                                                      ⎭
 -1 +1      110          120          130           140          150           160
                10
```

FIG. 4 (2)

```
CCA GGT GCT GGG GCT GGG GAA GAG TGG CCG GGG CTA GAG GGA GGA GGG CCC ATC GCC AGG GGT CGG AGG GTG GGG GCG CGT GCT GAG GCT CTG
GAG TCC AGA GGC CAG AAG GGA AAG GGT GGG GAG GAC CGA AGG TGG GCG CCA GGT GCC AGA ATG CCA GGT CCC TCC GTC TGA CGC TCC CTC TTC CCT
GGG GCT GGG ACA AGG CCC TCC TGT CCT CAG GCA CAG GGG CTG TGA CAA GGC CTT CAA CAC AGA ACC TGG AGC TG  AC  CCC TTG ACC TCC CTG ACC
                                                                                                intron 4
                                    170                180            190            200             210            220             230            240
CCT GAT CTG CTG TCC CTG CAG GAG CCT GGT GCC CAG ACT GCC CTG AAG AGT CAG ACC CCA GTC TCC AGA GAC CCC ACC CCA GAG CAG ACC CAC AGG
                        Glu Pro Gly Gly Gln Thr Ala Leu Lys Ser Pro Gly Val Cys Ser Arg Asp Pro Thr Pro Glu Gln Thr His Arg
                                             20                           30                                       40
                  250                 260            270           280            290            300              310            320            330
CTG GCC CGG GCC ATG ATG GCC TTC TCC GAC CTG TTC CTG GTG GCT CAA CTC CTG CTG GTC TCC ACC TGC ATC CTG TCA CCC AGT GTG
Leu Ala Arg Ala Met Met Ala Phe Ser Asp Leu Phe Leu Val Ala Gln Thr Ser Thr Cys Pro Asn Leu Ile Leu Ser Pro Leu Ser Val
                   50                              60                                   70
340      350                 360
GCC CTG CTG TCT CAC CTG GCA CTA GGT ATC CCA GTT TCC TAT CCT ATC TCT AGT CCA GCA CCA AGA GAG CTG GGA GCC........C
Ala Leu Ala Leu Ser His Leu Ala Leu G
                   80
                                          .........intron 5 (~1.5 kb).........C CGG CCT CAG CCT TCG GTG CCT CCA GGT GCT CAG
                                                                                                                Ty Ala Gln
                                                                                                                    470
         380           390           400           410            420            430           440            450            460
AAC CAC ACG TTG CAG AGG CTG CAA CAG GTG CTG CAC GCA GGG CCC TGC CTC CCC CAT CTG AGC CTG CAG GAC CGC CTC CAG GAC GGC CCC
Asn His Thr Leu Gln Arg Leu Gln Gln Val Leu His Ala Gly Pro Cys Leu Pro His Leu Ser Arg Leu Cys Gln Asp Leu Gly Pro
                    90                            100                                              110
          480             490            500              510
GCC GCG TTC CGA CTG GCT GCC AGG GCT CCT GCC AGG TAC CTG CAG TGA AAA GGT AGG CGC TGA CCC TCA GTC CTG CCC TGG GTG GAG GGT GAG
Gly Ala Phe Arg Leu Ala Ala Arg Met Tyr Leu Gln Lys G
                   120                            130
```

EXON V                                          EXON VI

FIG. 4 (3)

*Figure depicts a DNA and protein sequence spanning nucleotides 520–1060, with annotations indicating intron 6, intron 7 (~0.7 kb), intron 8 (~3.1 kb), intron 9 (~1.1 kb), and exons VII, VIII, and IX. Amino acid numbering runs from approximately 140 to 310.*

FIG. 4 (4)

```
                                                            ┌─────────── EXON X ───────────
              1070          1080          1090          1100          1110          1120          1130
CTG ACC ACC ATC TCT GCC CTG GCA GGC CTG CAG GAG TTC CAG GCC CCA GAC CTG CGT GGG ATC TCC GAG CAG AGC CTG GTG GTG TCC GGC GTG
Ty  Leu Gln Leu Phe Gln Glu Phe Gln Ala Pro Asp Leu Arg Gly Ile Ser Glu Gln Ser Leu Val Val Ser Gly Val
                                                                            330
         1140          1150          1160          1170          1180          1190          1200          1210          1220          1230
CAG CAT CAG TCC ACC CTG GAG CTC AGC GAG GTC GGC GTG GAG GCG GCG GCG GCC AGC ATT GCC ATG TCC CGC ATG TCC CTG TCC TTC AGC
Gln His Gln Ser Thr Leu Glu Leu Ser Glu Val Gly Val Glu Ala Ala Ala Ala Ser Ile Ala Met Ser Arg Met Ser Leu Ser Phe Ser
340                             350                             360                                         370
         1240          1250          1260          1270          1280          1290          1300          1310          1320
GTG AAC CGC CCC TTC CTC TTC ATC TTC GAG GAC ACA GGC CTT CCC GTG GCC GTG AGG AAC CCC AGT GCA CCG CGG
Val Asn Arg Pro Phe Leu Phe Ile Phe Glu Asp Thr Gly Leu Pro Val Gly Val Arg Asn Pro Ser Ala Pro Arg
                380                             390                                     400
         1330          1340          1350          1360          1370          1380          1390          1400          1410          1420
GAG CTC AAG CAA CAG CAG GAT TCC CGG GCC AAC AAG GAC TTC CAG AGC CTG AAA GCC TTC CCC CGA GAA GCT TTC GGC CTT GAC
Glu Leu Lys Gln Gln Gln Asp Ser Arg Ala Asn Lys Asp Phe Gln Ser Leu Lys Ala Phe Pro Arg Glu Ala Phe Gly Leu Asp
                                                                                                                        430
                410
         1430          1440          1450          1460          1470          1480          1490          1500          1510
AAA CTT GTG CCC ATG GAG GAT TAC CCC AGC CAG TTT GGC AGC CCC AAG TGA TCC AGA GTC CCT GCC TGG ACC AGC
Lys Leu Val Pro Met Glu Asp Tyr Pro Ser Gln Phe Gly Ser Pro Lys
                440                                         450

CTC TCC ACT CAT GTG ACT CTT TCC AAC CTG CTT TGT GGC ACT GGG GCA GGG GCC AGT CTG AGA GAG GCC ATT CTT TCC CAA CAC CTC TTG

GGG AGT TTA GGG TGG GGG CGG CTG GGA GGA GGG AGG TGC TTC TAG TGC CAG GAG ACA GTT TCC CCC ACG TCA GCT GGG ACA CCC CGA CTT

GTG TCC ACC GGG GCC TGG GCA GGA GGG AGG AGG GGG AGG GGG CTG CCT TTG TCC GGC AGC CTG CCT AGG GTG GAC GGG CCC TGG TGG TGG

TTG TTT ACC AGA GAA AAA GGG GTT GTC GTC CTC AGC CCT CCC CAG ACT TCC CGG CTC ACC CAG ACT TCC CGG AGA GAC GGG CCC ATC AGC CTC CAT

CTC GGG AGG CGA AGC CTG TGC TTG TCA GA ACC CAG CTC TTT TGT AAG GTT TGT GTA GTG ATT TTT ATG CCA CCT CCT

CCT ACC CCC TGT GGT TTT TTG CAC CGT GGT TTT TTG CAC CGT TCT CGC 2232

CTG CCC GGG AGC TCA GA ACC GAG GCA GGG AAG GAT CCC ATG AGC CTC TTA AGG CTC TTT TGT AAG GTT TGT GTA GTG ATT TTT ATG CCA CCT GAA

TAA AGA ATG AAT GGG CGC TGT GGT TTT TTG CAC CGT TCT CGC 2232
```

CDNA AND GENOMIC DNA ENCODING THE AMINO ACID SEQUENCE OF HUMAN α₂-PLASMIN INHIBITION

This application is a continuation of now abandoned application, Ser. No. 07/134,301 filed on Dec. 15, 1987, abandoned.

This invention relates to the amino acid sequence of a human $\alpha_2$-plasmin inhibitor (or $\alpha_2$-antiplasmin), and cDNA and genomic DNA encoding this sequence.

The human $\alpha_2$-plasmin inhibitor was first isolated and purified by Aoki and Moroi. It is known to be a strong plasmin inhibitor which instantaneously inhibits the esterase activity of plasmin, a fibrinolytic enzyme, and is a single-chain glycoprotein having a molecular weight of about 67,000 and containing 11.7% of sugar chains [M. Moroi & N. Aoki: The Journal of Biological Chemistry, 251, 5956-5965 (1976)].

On the other hand, it is known that the human $\alpha_2$-plasmin inhibitor has three types of active sites. One is a site of inhibiting the protrolytic action of plasmin (to be referred to sometimes as the "reactive site"). A second is a site of binding to plasmin at the carboxyl terminal portion B. Wiman & D. Collen: European Journal of Biochemistry, 84, 573-578 (1978)]. A third is a site of binding to fibrin [Y. Sakata et al.: Thrombosis Research, 16, 279-282 (1979)].

It has already been determined that among the three active sites of the human $\alpha_2$-plasmin inhibitor, the fibrin binding site is Gln which is the second amino acid from the amino terminus of the human $\alpha_2$-plasmin inhibitor [T. Tamaki & N. Aoki: The Journal of Biological Chemistry, 257, 14767-14772 (1982)]. A peptide fragment composed of 26 amino acids including the plasmin binding site is also known. It has been reported that this peptide fragment exists near the carboxy-terminus of the human $\alpha_2$-plasmin inhibitor [see T. Sasaki et al.: The Journal of Biochemistry, 99, 1699-1705 (1986)], but its position is not clear. It has been reported that the reactive site of the human $\alpha_2$-plasmin inhibitor is Leu-Met [see B. Wiman Chemistry, 254, 9291-9297 (1979)], or it is described that this reactive site is Arg-Met [see H. R. Lijnen et al.: Thrombosis Research, 39, 625-630 (1985)]. But its position has not yet been determined clearly. If the structures and positions of these plasmin binding sites and the reactive site and their vicinities are determined, it will be very beneficial and interesting to the utilization and development of human $\alpha_2$-plasmin inhibitor.

On the other hand, if a DNA of human $\alpha_2$-plasmin inhibitor or its fragment is obtained, it will become possible to produce part or the whole of the human $\alpha_2$-plasmin inhibitor by a gene manipulation technique. The utilization of such a gene or its fragment will permit diagnosis of human $\alpha_2$-plasmin inhibitor deficiency.

As a result of studies on human $\alpha_2$-plasmin inhibitor gene, the present inventors isolated complementary DNA (to be referred to as cDNA) of human $\alpha_2$-plasmin inhibitor containing 1209 nucleotides coding for the sequence of 403 amino acids from the carboxy-terminus of the human $\alpha_2$-plasmin inhibitor, and elucidated the detailed structure of the human $\alpha_2$-plasmin inhibitor on the carboxy-terminus side by analyzing the base sequence of the cDNA of human $\alpha_2$-plasmin inhibitor. This has led to the present invention.

Specifically, according to one aspect of this invention, there is provided cDNA encoding a human $\alpha_2$-plasmin inhibitor precursor represented by the sequence of amino acids from the $-39$th Met to the 452nd Lys in FIG. 1 of the accompanying drawings, preferably cDNA represented by the base sequence from the 7th A to the 1479th G in FIG. 1. The invention also provides an amino acid sequence of a human $\alpha_2$-plasmin inhibitor precursor represented by the sequence of 452 amino acids from the $-39$th Met to the 452nd Lys in FIG. 1.

In the amino acid sequence composed of 491 amino acids shown in FIG. 1, the amino acid sequence from the 1st Asn to the 452nd Lys shows the protein of the human $\alpha_2$-plasmin inhibitor itself, and the amino acid sequence from the $-39$th Met to the $-1$st Pro shows the leader sequence.

The present inventors furthered their studies on the elucidation of the structure of a genomic DNA coding for the human $\alpha_2$-plasmin inhibitor, and isolated human genomic DNAs coding for an amino acid sequence composed of 39 amino acids and corresponding to the propeptide of human $\alpha_2$-plasmin inhibitor and an amino acid sequence composed of 452 amino acids and constituting the human $\alpha_2$-plasmin inhibitor. Analysis of the base sequences of these amino acids has led to the discovery that the genomic DNA is a DNA composed of exons II, III, IV, V, VI, VII, VIII, IX and X, as shown in FIG. 4, bonded to each other via introns and encoding human $\alpha_2$-plasmin inhibitor protein, and that exon I shown in FIG. 4 is further bonded to the upstream end of exon II via an intron.

Thus, according to another aspect of this invention, there is provided a genomic DNA composed of 9 exons from exon II to X and 8 introns interposed between the adjoining exons, or a genomic gene consisting of the above genomic gene and an exon I bonded to the upstream end of the exon II via an intron.

Part of exon II, exon III and part of exon IV in the genomic DNA of the invention encode a propeptide of 39 amino acids. The remaining part of exon IV, exon V, exon VI, exon VII, exon VII, exon VIII, exon IX and part of exon X encode human $\alpha_2$-plasmin inhibitor. The restriction endonuclease map of the genomic DNA of the human $\alpha_2$-plasmin inhibitor with regard to six restriction endonucleases is shown in FIG. 3 (2). This genomic gene was obtained as clones of three lambda phages shown in FIG. 3 (3).

The base sequence and amino acid sequence of the genomic DNA of human $\alpha_2$-plasmin inhibitor are shown in FIG. 4. In FIG. 4, the exons are the underlined portions of the base sequence. Exon I does not encode the amino acid sequence. Exon II consists of 67 bases in total, four bases (GAAC) in the non-coding region and 63 bases encoding 21 amino acids in part of the propeptide. Exon III consists of 39 bases encoding 13 amino acids in part of the propeptide. Exon IV consists of 63 bases in total, 15 bases encoding 5 amino acids in part of the propeptide and 48 based encoding 16 amino acids in the N-terminus portion of the $\alpha_2$-plasmin inhibitor. Exon V consists of 202 bases encoding 67 1/3 amino acids of $\alpha_2$-plasmin inhibitor. Exon VI consists of 144 bases encoding 48 amino acids of $\alpha_2$-plasmin inhibitor. Exon VII consists of 204 bases encoding 68 amino acids of $\alpha_2$-plasmin inhibitor. Exon VIII consists of 143 bases encoding 47 2/3 amino acids of $\alpha_2$-plasmin inhibitor. Exon IX consists of 205 bases encoding 68 1/3 amino acids of $\alpha_2$-plasmin inhibitor. Exon X consists of 1160 bases in total, 410 bases encoding 136 2/3 amino acids on the C-terminus of $\alpha_2$-plasmin inhibitor and 759 bases in the non-coding region. The DNA base sequences of these exons are underlined.

The following Examples illustrate isolation of messenger RNA ("mRNA" for short) from human liver cells, construction of a cDNA library, screening of human $\alpha_2$-plasmin inhibitor, recloning of human $\alpha_2$-plasmin inhibitor cDNA, preparation of a restriction endonuclease cleavage map of human $\alpha_2$-plasmin inhibitor, determination of the base sequence of human $\alpha_2$-plasmin inhibitor cDNA, cloning of human $\alpha_2$-plasmin inhibitor genomic DNA, preparation of a restriction endonuclease map of the human $\alpha_2$-plasmin inhibitor genomic DNA, and determination of the base sequence of the human $\alpha_2$-plasmin inhibitor genomic DNA in detail.

It should be understood that in the present specification and the accompanying drawings, amino acids and polypeptides are abbreviated by the method of IUPAC-IUB, Commission on Biological Nomenclature (CBN). For example, the following abbreviations are used.

Ala: L-alanine
Arg: L-arginine
Asn: L-asspargine
Asp: L-aspartic acid
Cys: L-cysteine
Gln: L-glutamine
Glu: L-glutamic acid
Gly: glycine
His: L-histidine
Ile: L-isoleucine
Leu: L-leucine
Lys: L-lysine
Met: L-methionine
Phe: L-phenylalanine
Pro: L-proline
Ser: L-serine
Thr: L-threonine
Trp: L-tryptophan
Tyr: L-tyrosine
Val: L-valine The DNA sequence will be shown in abbreviations by bases contained in the constituent deoxyribonucleotides. For example, the following abbreviations are used.

A: adenine (representing deoxyadenylic acid)
C: cytosine (representing deoxycytidylic acid)
G: guanine (representing deoxyguanylic acid)
T: thymine (representing deoxythymidylic acid)

BRIEF DESCRIPTION OF THE ACCOMPANYING DRAWINGS

FIG. 1 shows the amino acid sequence of human $\alpha_2$-plasmin inhibitor in this invention and a cDNA thereof.

Figure 3:
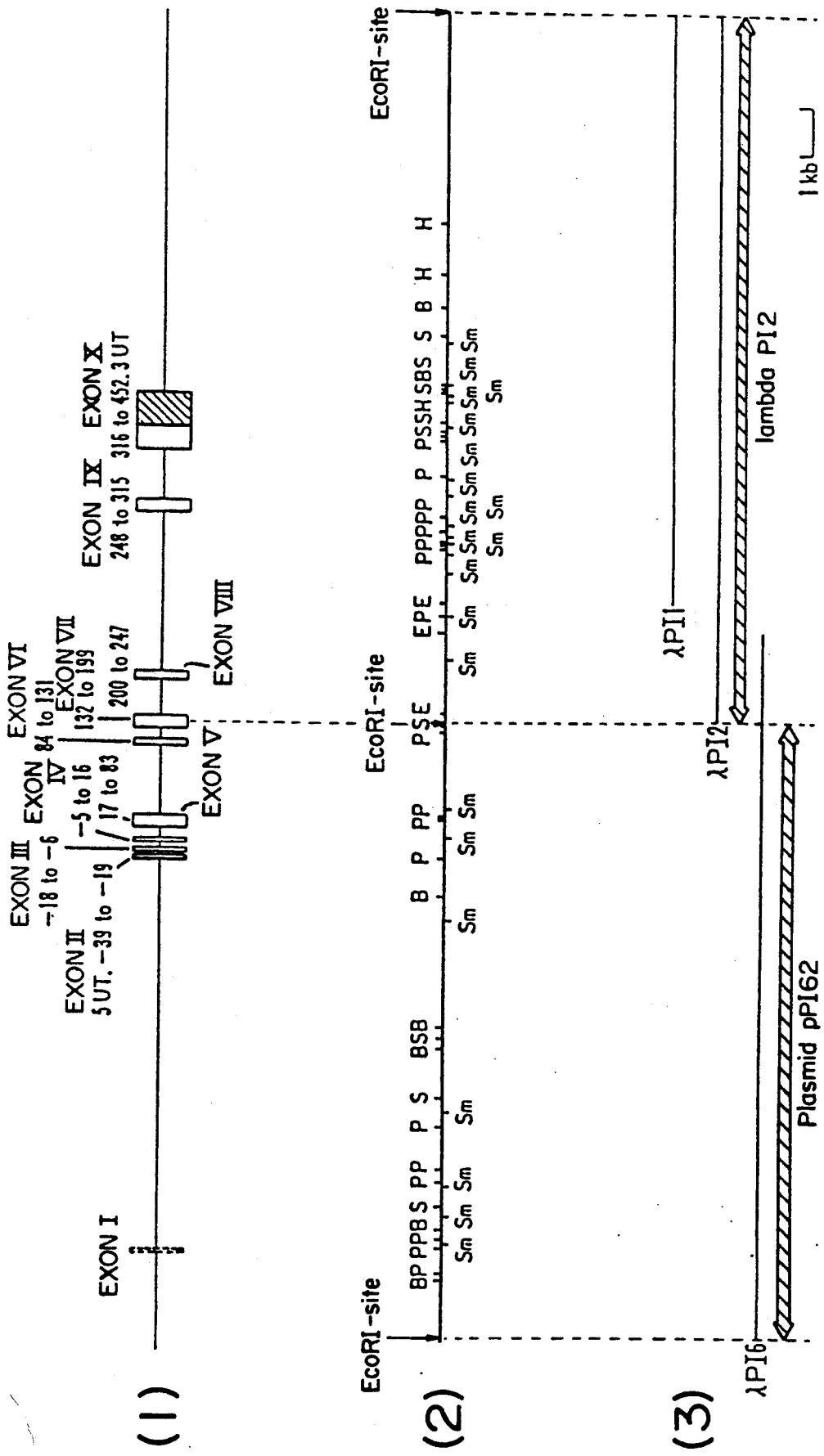

FIG. 3 (1) shows introns-exons of the genomic DNA of human $\alpha_2$-plasmin inhibitor. The ten exons are shown by rectangles. Exon I, part of exon II and part of exon X are non-coding regions which do not encode amino acids. The non-coding region of exon X is shown by hatchings.

FIG. 3 (2) is a restriction endonuclease map of the genomic DNA of human $\alpha_2$-plasmin inhibitor in accordance with this invention. The symbols show the following endonucleases.

B: BamHI
E: EcoRI
H: HindIII
P: PstI
S: SacI
Sm: SmaI

FIG. 3 (3) shows DNA fragments in phage clones encoding the genomic DNA of human $\alpha_2$-plasmin inhibitor in accordance with this invention. This figure also shows the sequence of a pUC19 plasmid, pP162, and charon 4A phage, lambda P12, encoding separate portions of the genomic DNA of the invention. The plasmid and phage were deposited with the American Type Culture Collection, 12301 Parklawn Drive, Rockville, Md. 20852 on Nov. 13, 1991 under the Budapest Treaty and bear ATCC Designation Nos. 75142 and 75143, respectively.

FIGS. 3 (1) to (3) correspond to each other vertically.

FIG. 4 shows the DNA base sequence and amino acid sequence of the genomic DNA of human $\alpha_2$-plasmin inhibitor in accordance with this invention. The exon portions are underlined, and the corresponding amino acids are indicated beneath. A sequence presumably corresponding to the TATA box upstream of exon I and the transcriptional site are surrounded by lines. The polyadenylation recognition site downstream of 3'-terminus is surrounded by a line.

EXAMPLE 1

Isolation of mRNA from human liver cells mRNA was isolated from human liver cells in accordance with the guanidine thiocyanate method [see J. M. Chirgwin et al.: Biochemistry, 18, 5294–5299 (1979)]. To $2 \times 10^8$ human liver cells was added 5 ml of GTC solution (6M guanidine isothiocyanate, 5mM sodium citrate, 0.1M 20-mercaptoethanol, 0.5% sodium N-lauroylsarcosinate), and the mixture was homogenized. The homogenate was superimposed on 3.8 ml of an aqueous solution containing 5.7M CsCl and 0.1M EDTA. They were ultracentrifuged using an RPS-50T rotor (Hitachi) at 35,000 rpm for 15 hours. After ultracentrifugation, the solution was carefully removed, and the residue was rinsed three times with about 1 ml of ethanol, and dissolved in 1.4 ml of water. The solution was treated with ethanol to form a precipitate. The precipitate was dissolved in 0.5 ml of a washing solution composed of 0.5M NaCl, 18mM of Tris-HCl (pH 7.5), 1mM EDTA and 0.05% of SDS, and the solution was passed through 0.5 ml of Oligo(dT) cellulose column. The column was washed with the above washing solution, and eluted with an eluent composed of 10mM Tris-HCl (pH 7.5), 1mM EDTA and 0.05% SDS to give about 31 micrograms of polyA+mRNA.

EXAMPLE 2

Construction of cDNA library cDNA was synthesized from the polyA+mRNA derived from human liver cells by the method of Gubler and Hoffman [see U. Gubler & B. J. Hoffman: Gene, 25, 263–269 (1983)] using a cDNA synthesis kit made by Amersham Co.

A single-stranded cDNA was synthesized in a yield of about 30% by adding 5 micrograms of Oligo(dT) 12-18 to 5 micrograms of polyA+mRNA in the presence of 50 units of RNase inhibiting enzyme (HPRI) derived from human placenta and causing transcriptase to act at 42° C. for 1.5 hours. Four units of E. coli ribonuclease H and 115 units of *E. coli* DNA polymerase I were added to the resulting reaction solution, and reacted at 12° C. for 1 hour and then at 22° C. for 1 hour. The reaction mixture was left to stand at 70° C. for 10 minutes to deactivate the enzymes. Then, 10 units of T4-DNA polymerase was added and reacted at 47° C. for 10 minutes to obtain a double-stranded cDNA in a yield of about 95%. The double-stranded cDNA was reacted with 20 units of EcoRI methylase at 37° C. for 1 hour. To the reaction product was bonded 16 units of EcoRI (made by Takara Shuzo). Then, 16 units of EcoRI (made by Takara Shuzo) was added and the mixture was reacted at 37° C. for 2 hours. The reaction mixture was passed through a column of Sephasrose L-4B to purify it and 0.34 microgram of cDNA was obtained. This cDNA (0.4 microgram) and 1.0 microgram of λgt10 arm (made by Vector Cloning Systems) were ligated to obtain a hybrid DNA having the cDNA derived from human liver cells inserted into it. The resulting hybrid DNA was packaged in vitro [see A. Becker & M. Gold: Proc. Natl. Acad. Sci. USA, 72, 581 (1975)] to obtain a cDNA library derived from human liver cells.

EXAMPLE 3

Screening of human $\alpha_2$-plasmin inhibitor cDNA

The library of cDNA derived from human liver cells obtained in Example 2 was transfected into *E. coli* C 600 hfl⁻strain to form plaques. Clones containing human $\alpha_2$-plasmin inhibitor DNA were selected in accordance with the Benton and Davis plaque hybridization method using synthetic DNAs P-1 and P-2 labelled with [$^{32}$P] [see W. D. Benton & R. W. Davis: Science, 196, 180 (1977)]. The synthetic DNAs used as probes were synthesized by using a DNA sequence corresponding to the partial amino acid sequence of human $\alpha_2$-plasmin inhibitor reported by Collen et al. [see D. Collen et al.: Thrombosis and Haemostasis, 48, 311–314 (1982)] as a DNA synthesizer (made by Applied Biosystems).

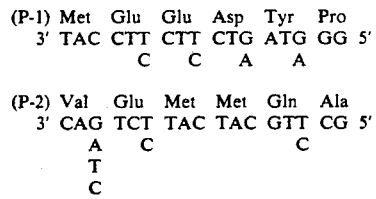

EXAMPLE 4

Recloning of human $\alpha_2$-plasmin inhibitor cDNA

Plasmid pUC8 (2 micrograms) was digested with restriction endonuclease EcoRI in accordance with Example 2, and 1.9 units of alkaline phosphatase (*E. coli* C75: a product of Takara Shuzo) was added. The mixture was reacted at 58° C. for 2 hours. After the reaction, the reaction solution was extracted with phenol three times to deactivate and remove the alkaline phosphatase in the reaction solution. The EcoRI-digested cDNA fragment of human $\alpha_2$-plasmin inhibitor obtained in Example 3 was added to the resulting EcoRI-/alkaline phosphatase treated solution of pUC8, and 2 units of T4-DNA ligase was reacted with the mixture at 12° C. for 16 hours to perform ligation.

*E. coli* LE 392 was transformed with hybrid DNA prepared by ligating the EcoRI-digested cDNA fragment of human $\alpha_2$-plasmin inhibitor in accordance with an ordinary CaCl$_2$ method [see M. V. Norgard et al.: Gene, 3, 297 (1978)]. The transformants were inoculated in L-broth plates containing ampicillin in a concentration of 50 micrograms/ml. The plates were cultivated overnight at 37° C. to grow the transformants. DNAs were prepared from the resulting colonies by a known method, and by agarose gel electrophoresis, the desired hybrid DNAs were determined. They were named pPI 41, pPI 39 and pPI 142.

EXAMPLE 5

Preparation of a restriction endonuclease map of human $\alpha_2$-plasmin inhibitor cDNA Lambda gt10DNA containing the human $\alpha_2$-plasmin inhibitor cDNA obtained in Example 3 was digested with EcoRI to cut out the inserted human $\alpha_2$-plasmin inhibitor cDNA and isolated by 0.8% agarose gel electrophoresis. This human $\alpha_2$-plasmin inhibitor cDNA fragment (0.1 microgram) was dissolved in 10 microliters of a buffer for restriction endonucleases an aqueous solution containing 100mM NaCl, 50mM Tris-HCl (pH 7.5), 10mM MgCl$_2$ and 1mM dithiothreitol for digestion with EcoRI; an aqueous solution containing 50mM NaCl, 10mM Tris-HCl (pH 7.5), 10mM MgCl$_2$ and 1mM dithiothreitol for digestion with BamHI, PstI and HindIII; and an aqueous solution containing 20mM KCl, 10mM Tris-HCl (pH 8.0), 10mM MgCl$_2$ and 1mM dithiothreitol for digestion with SmaI, respectively], and digested at 37° C. for 1 hour. When the digestion was carried out using two restriction endonucleases, the cDNA fragment was first treated with one restriction endonuclease which acted at a low salt concentration. Then, the salt concentration was raised to a predetermined concentration, and the DNA fragment was treated with the other enzyme which acted at a high salt concentration.

Figure 2:
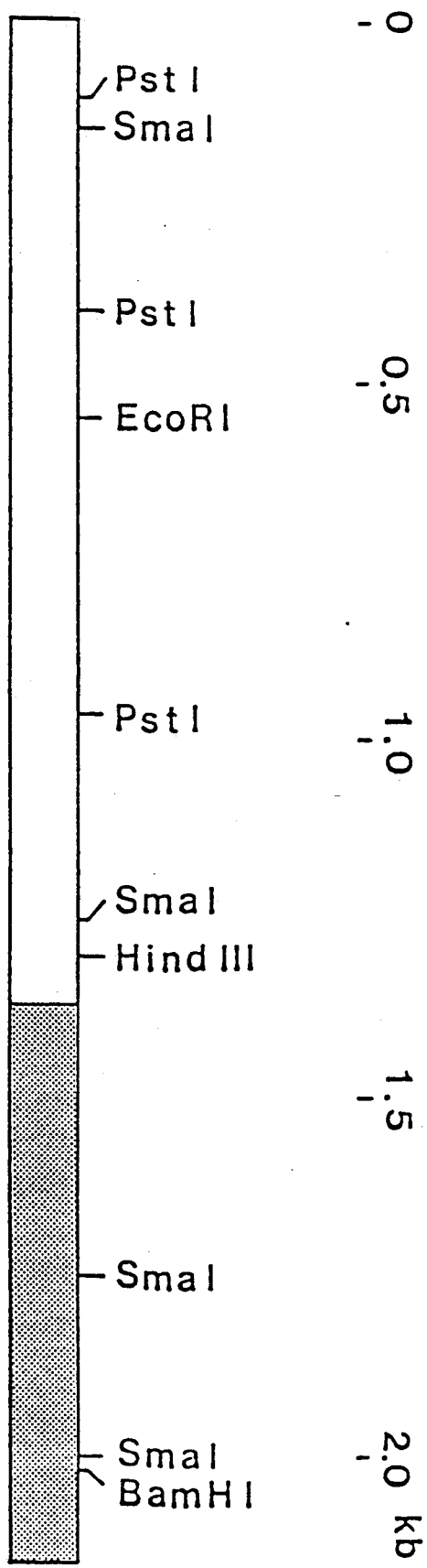
FIG. 2 is a restriction endonuclease map of the cDNA of human $\alpha_2$-plasmin inhibitor. The white portion is a coding region of the amino acid sequence of the invention and the black portion is a non-coding region.

After digestion, 1 microliter of 0.25% bromophenol blue and a 50% aqueous solution of glycerol were added, and the mixture was subjected to electrophoresis using 0.8%–1.2% agarose containing 1 microgram/ml of ethidium bromide. At the time of electrophoresis, a digestion product of the DNA of lambda phage with HindIII was used as a molecular size marker for the DNA fragment. After the electrophoresis, ultraviolet light was irradiated on the gel, and the digestion pattern was observed. The patterns of digestions with various restriction endonucleases alone or combinations of two restriction endonucleases were analyzed. The restriction endonuclease map thus obtained of the human $\alpha_2$-plasmin inhibitor cDNA having a molecular size of about 2.2 Kb is shown in FIG. 2.

EXAMPLE 6

Determination of the base sequence of human $\alpha_2$-plasmin inhibitor cDNA

The base sequence of the human $\alpha_2$-plasmin inhibitor cDNA was determined by the Sanger's dideoxy sequence method [see F. Sanger et al.: Proc. Natl. Acad. Sci. USA, 74, 5463–5467 (1977)].

For example, The EcoRI fragment of the human $\alpha_2$-plasmin inhibitor cDNA was inserted into the EcoRI site of M13 mp18 or M13 mp19 vector, and *E. coli* JM105 strain was transformed with the vector. A single-stranded hybrid DNA was prepared by a known method using the transformed JM105. The single-stranded DNA was subjected to sequence reaction using an M13 sequence kit (made by Amersham), and then subjected to electrophoresis using 6% polyacrylamide gel containing 7M urea. The gel was radioautographed overnight at −80° C. The separation pattern was analyzed to obtain data for determination of the base sequence of human $\alpha_2$-plasmin inhibitor.

As a result, the base sequence encoding the human $\alpha_2$-plasmin inhibitor was determined, and is shown in FIG. 1.

EXAMPLE 7

Cloning of human $\alpha_2$-plasmin inhibitor genomic DNA

DNA extracted from human placenta was digested with restriction endonucleases AluI and HaeIII, and inserted into Charon 4A bacteriophage vector arm via an EcoRi linker to construct a library. The plaques ($1.2 \times 10^6$) of the library were screened using cDNA fragments corresponding to an amino acid sequence from the 31st to the 130th amino acids from the N-terminus of the amino acid sequence of $\alpha_2$-plasmin inhibitor and a cDNA fragment corresponding to the 179th to the 429th amino acids from the N-terminus of the amino acid sequence of $\alpha_2$-plasmin inhibitor as probes [see W. D. Benton & R. W. Davis: Science, 196, 180–182 (1977)]. For the screening of clones upstream of 3', a synthetic DNA (5'ACTCCCCTGCCAGCC3') composed of 15 bases was used as a probe. When cDNAs were used as probes, the cDNA fragments were labelled with $^{32}$P by nick translation. The synthetic DNA was labelled on the 5' side with T4 polynucleotidekinase.

As a result of screening, three clones, λPI1, λPI2 and λPI6, encoding the entire region of the genomic DNA of $\alpha_2$-plasmin inhibitor were obtained. The correspondence of the clones to the genomic DNA is shown in FIGS. 3 (1), (2) and (3).

EXAMPLE 8

Preparation of a restriction endonuclease cleavage map of human $\alpha_2$-plasmin inhibitor genomic DNA The phage DNA containing human $\alpha_2$-plasmin inhibitor genomic DNA obtained in Example 7 was digested with EcoRI, and the inserted human $\alpha_2$-plasmin inhibitor genomic DNA was cut out and isolated by 0.9–1.5% agarose gel electrophoresis. This human $\alpha_2$-plasmin inhibitor DNA fragment (0.1 to 0.5 microgram) was dissolved in 10 microliters of a buffer for restriction endonucleases and digested with 2 units of various restriction endonucleases at 37° C. for 1 hour.

When digestion was carried out using two restriction endonucleases, the DNA fragment was first treated with one restriction endonuclease which acted at a low salt concentration. Then, the salt concentration was raised to a predetermined concentration, and the DNA fragment was treated with the other restriction endonuclease which acted at a high salt concentration.

After digestion, 1 microliter of 0.25% bromophenol blue and a 50% aqueous solution of glycerol were added, and the mixture was subjected to electrophoresis using 0.8%–1.2% agarose containing 1 microgram/ml of ethidium bromide. At the time of electrophoresis, a digestion product of the DNA of lambda phage with HindIII was used as a molecular size marker for the DNA fragment. After the electrophoresis, ultraviolet light was irradiated on the gel, and the digestion pattern was observed. The patterns of digestions with various restriction endonucleases alone or combinations of two restriction were analyzed. The resulting restriction endonuclease map of human $\alpha_2$-plasmin inhibitor genomic DNA so obtained is shown in FIG. 3 (2).

EXAMPLE 9

Determination of the base sequence of human $\alpha_2$-plasmin inhibitor genomic DNA The base sequence of the human $\alpha_2$-plasmin inhibitor genomic DNA was determined by the Sanger's dideoxy sequence method [see F. Sanger et al.: Proc. Natl. Acad. Sci. USA, 74, 5463–5467 (1977)].

For example, The EcoRI fragment of the human $\alpha_2$-plasmin inhibitor genomic DNA was inserted into the EcoRI site of M13 mp18 or M13 mp19 vector, and E. coli JM105 strain was transformed with the vector. A single-stranded hybrid DNA was prepared by a known method using the transformed JM105. The single-stranded DNA was subjected to sequence reaction using an M13 sequence kit (made by Amersham), and then subjected to electrophoresis using 6% polyacrylamide gel containing 7M urea. The gel was radioautographed overnight at −80° C. The separation pattern was analyzed to obtain data for determination of the base sequence of human $\alpha_2$-plasmin inhibitor.

As a result, the base sequence of the genomic DNA encoding the human $\alpha_2$-plasmin inhibitor was determined, and is shown in FIG. 4.

What is claimed is:

1. cDNA encoding a human $\alpha_2$-plasmin inhibitor precursor protein which consists of the following amino acid sequence:

```
                                              GAG    3
        −39
    Met Ala Leu Leu Trp Gly Leu Leu Val Leu Ser
    AACATGGCGCTGCTCTGGGGGCTCCTGGTGCTCAGC

−21
                    Trp Ser Cys Leu Gln Gly Pro Cys
                    TGGTCCTGCCTGCAAGGCCCCTGC      63
    −20
    Ser Val Phe Ser Pro Val Ser Ala Met Glu Pro Leu
    TCCGTGGGCTCCCCTGTGAGCGCCATGGAGCCCTTG

−1
                       Gly Arg Gln Leu Thr Ser Gly Pro
                       GGCCGGCAGCTAACTAGCGGGCCG    123
    +1
    Asn Gln Glu Gln Val Ser Pro Leu Thr Leu Leu Lys
    AACCAGGAGCAGGTGTCCCCACTTACCCTCCTCAAG

20
                      Leu Gly Asn Gln Glu Pro Gly Gly
                      TTGGGCAACCAGGAGCCTGGTGGC    183
    Gln Thr Ala Leu Lys Ser Pro Pro Gly Val Cys Ser
    CAGACTGCCCTGAAGAGTCCCCCAGGAGTCTGCAGC

40
                          Arg Asp Pro Thr Pro Glu Gln Thr
                          AGAGACCCCACCCCAGAGCAGACC  243
    His Arg Leu Ala Arg Ala Met Met Ala Phe Thr Ala
    CACAGGCTGGCCCGGGCCATGATGGCCTTCACTGCC

60
                              Asp Leu Phe Ser Leu Val Ala Gln
                              GACCTGTTCTCCCTGGTGGCTCAA   303
    Thr Ser Thr Cys Pro Asn Leu Ile  Leu Ser Pro Leu
    ACGTCCACCTGCCCCAACCTCATCCTGTCACCCCTG
```

```
                                    80
            Ser Val Ala Leu Ala Leu Ser His
            AGTGTGGCCCTGGCGCTGTCTCAC    363

Leu Ala Leu Gly Ala Gln Asn His Thr Leu Gln Arg
CTGGCACTAGGTGCTCAGAACCACACGTTGCAGAGG
                                    100
            Leu Gln Gln Val Leu His Ala Gly
            CTGCAACAGGTGCTGCACGCAGGC    423

Ser Gly Pro Cys Leu Pro His Leu Leu Ser Arg Leu
TCAGGGCCCTGCCTCCCCCATCTGCTGAGCCGCCTC
                                    120
                  Cys Gln Asp Leu Gly Pro Gly Ala
                  TGCCAGGACCTGGGCCCCGGCGCG    483

Phe Arg Leu Ala Ala Arg Met Tyr Leu Gln Lys Gly
TTCCGACTGGCTGCCAGGATGTACCTGCAGAAAGGA
                                    140
               Phe Pro Ile Lys Glu Asp Phe Leu
               TTTCCCATCAAAGAAGATTTCCTG    543

Glu Gln Ser Glu Gln Leu Phe Gly Ala Lys Pro Val
GAACAATCCGAACAGCTATTTGGGGCAAAGCCCGTG
                                    160
                  Ser Leu Thr Gly Lys Gln Glu Asp
                  AGCCTGACGGGAAAGCAGGAAGAT    603

Asp Leu Ala Asn Ile Asn Gln Trp Val Lys Glu Ala
GACCTGGCAAACATCAACCAATGGGTGAAGGAGGCC
                                    180
                  Thr Glu Gly Lys Ile Gln Glu Phe
                  ACGGAGGGGAAGATTCAGGAATTC    663

Leu Ser Gly Leu Pro Glu Asp Thr Val Leu Leu Leu
CTCTCTGGGCTGCCGGAAGACACCGTGTTGCTTCTC
                                    200
                     Leu Asn Ala Ile His Phe Gln Gly
                     CTCAACGCCATCCACTTCCAGGGT    723

Phe Trp Arg Asn Lys Phe Asp Pro Ser Leu Thr Gln
TTCTGGAGGAACAAGTTTGACCCGAGCCTTACCCAG
                                    220
                     Arg Asp Ser Phe His Leu Asp Glu
                     AGAGACTCCTTCCACCTGGACGAG    783

Gln Phe Thr Val Pro Val Gln Met Met Gln Ala Arg
CAGTTCACGGTGCCCGTGGAAATGATGCAGGCCCGC
                                    240
                     Thr Tyr Pro Leu Arg Trp Phe Leu
                     ACGTACCCGCTGCGCTGGTTCTTG    843

Leu Glu Gln Pro Glu Ile Gln Val Ala His Phe Pro
CTGGAGCAGCCTGAGATCCAGGTGGCTCATTTCCCC
                                    260
                        Phe Lys Asn Asn Met Ser Phe Val
                        TTTAAGAACAACATGAGCTTTGTG    903

Val Leu Val Pro Thr His Phe Glu Trp Asn Val Ser
GTCCTTGTACCCACCCACTTTGAATGGAACGTGTCC
                                    280
            Gln Val Leu Ala Asn Leu Ser Trp
            CAGGTACTGGCCAACCTGAGTTGG    963

Asp Thr Leu His Pro Pro Leu Val Trp Glu Arg Pro
GACACCCTGCACCCACCTCTGGTGTGGGAGAGGCCC
                                    300
                     Thr Lys Val Arg Leu Pro Lys Leu
                     ACCAAGGTCCGGCTGCCTAAGCTG    1023

Tyr Leu Lys His Gln Met Asp Leu Val Ala Thr Leu
TATCTGAAACACCAAATGGACCTGGTGGCCACCCTC
                                    320
                        Ser Gln Leu Gly Leu Gln Glu Leu
                        AGCCAGCTGGGCCTGCAGGAGTTG    1083

Phe Gln Ala Pro Asp Leu Arg Gly Ile Ser Glu Gln
TTCCAGGCCCCAGACCTGCGTGGGATCTCCGAGCAG
                                    340
                        Ser Leu Val Val Ser Gly Val Gln
                        AGCCTGGTGGTGTCCGGCGTGCAG    1143

His Gln Ser Thr Leu Glu Leu Ser Glu Val Gly Val
CATCAGTCCACCCTGGAGCTCAGCGAGTGCGGCGTG
                                    360
                           Glu Ala Ala Ala Thr Ser Ile
                           GAGGCGGCGGCGGCCACCAGCATT    1203

Ala Met Ser Arg Met Ser Leu Ser Ser Phe Ser Val
GCCATGTCCCGCATGTCCCTGTCCTCCTTCAGCGTG
                                    380
                              Asn Arg Pro Phe Leu Phe Phe Ile
                              AACCGCCCCTTCCTCTTCTTCATC    1263

Phe Glu Asp Thr Thr Gly Leu Pro Leu Phe Val Gly
TTCGAGGACACCACAGGCCTTCCCCTCTTCGTGGGC
                                    400
                              Ser Val Arg Asn Pro Asn Pro Ser
                              AGCGTGAGGAACCCCAACCCCAGT    1323

Ala Pro Arg Glu Leu Lys Glu Gln Gln Asp Ser Pro
GCACCGCGGGAGCTCAAGGAACAGCAGGATTCCCCG
                                    420
                           Gly Asn Lys Asp Phe Leu Gln Ser
                           GGCAACAAGGACTTCCTCCAGAGC    1383

Leu Lys Gly Phe Pro Arg Gly Asp Lys Leu Phe Gly
CTGAAAGGCTTCCCCCGCGGAGACAAGCTTTTCGGC
                                    440
                              Pro Asp Leu Lys Leu Val Pro Pro
                              CCTGACTTAAAACTTGTGCCCCCC    1443
                                    452
            Met Glu Glu Asp Tyr Pro Gln Phe Gly Ser Pro Lys
            ATGGAGGAGGATTACCCCCAGTTTGGCAGCCCCAAG
```

2. The cDNA of claim 1 which consists of the following base sequence:

```
        -39                                                          -21
        Met Ala Leu Leu Trp Gly Leu Leu Val Leu Ser Trp Ser Cys Leu Gln Gly Pro Cys
        ATGGCGCTGCTCTGGGGGCTCCTGGTGCTCAGCTGGTCCTGCCTGCAAGGCCCCTGC        60

-20                                                          -1
        Ser Val Phe Ser Pro Val Ser Ala Met Glu Pro Leu Gly Arg Gln Leu Thr Ser Gly Pro
        TCCGTGGGCTCCCCTGTGAGCGCCATGGAGCCCTTGGGCCGGCAGCTAACTAGCGGGCCG    120
```

-continued

```
+1                                                                                    20
Asn Gln Glu Gln Val Ser Pro Leu Thr Leu Leu Lys Leu Gly Asn Gln Glu Pro Gly Gly
AACCAGGAGCAGGTGTCCCCACTTACCCTCCTCAAGTTGGGCAACCAGGAGCCTGGTGGC                        180

40
Gln Thr Ala Leu Lys Ser Pro Pro Gly Val Cys Ser Arg Asp Pro Thr Pro Glu Gln Thr
CAGACTGCCCTGAAGAGTCCCCCAGGAGTCTGCAGCAGAGACCCCACCCCAGAGCAGACC                        240

60
His Arg Leu Ala Arg Ala Met Met Ala Phe Thr Ala Asp Leu Phe Ser Leu Val Ala Gln
CACAGGCTGGCCCGGGCCATGATGGCCTTCACTGCCGACCTGTTCTCCCTGGTGGCTCAA                        300

80
Thr Ser Thr Cys Pro Asn Leu Ile Leu Ser Pro Leu Ser Val Ala Leu Ala Leu Ser His
ACGTCCACCTGCCCCAACCTCATCCTGTCACCCCTGAGTGTGGCCCTGGCGCTGTCTCAC                        360

100
Leu Ala Leu Gly Ala Gln Asn His Thr Leu Gln Arg Leu Gln Gln Val Leu His Ala Gly
CTGGCACTAGGTGCTCAGAACCACACGTTGCAGAGGCTGCAACAGGTGCTGCACGCAGGC                        420

120
Ser Gly Pro Cys Leu Pro His Leu Leu Ser Arg Leu Cys Gln Asp Leu Gly Pro Gly Ala
TCAGGGCCCTGCCTCCCCCATCTGCTGAGCCGCCTCTGCCAGGACCTGGGCCCCGGCGCG                        480

140
Phe Arg Leu Ala Ala Arg Met Tyr Leu Gln Lys Gly Phe Pro Ile Lys Glu Asp Phe Leu
TTCCGACTGGCTGCCAGGATGTACCTGCAGAAAGGATTTCCCATCAAAGAAGATTTCCTG                        540

160
Glu Gln Ser Glu Gln Leu Phe Gly Ala Lys Pro Val Ser Leu Thr Gly Lys Gln Glu Asp
GAACAATCCGAACAGCTATTTGGGGCAAAGCCCGTGAGCCTGACGGGAAAGCAGGAAGAT                        600

180
Asp Leu Ala Asn Ile Asn Gln Trp Val Lys Glu Ala Thr Glu Gly Lys Ile Gln Glu Phe
GACCTGGCAAACATCAACCAATGGGTGAAGGAGGCCACGGAGGGGAAGATTCAGGAATTC                        660

200
Leu Ser Gly Leu Pro Glu Asp Thr Val Leu Leu Leu Leu Asn Ala Ile His Phe Gln Gly
CTCTCTGGGCTGCCGGAAGACACCGTGTTGCTTCTCCTCAACGCCATCCACTTCCAGGGT                        720

220
Phe Trp Arg Asn Lys Phe Asp Pro Ser Leu Thr Gln Arg Asp Ser Phe His Leu Asp Glu
TTCTGGAGGAACAAGTTTGACCCGAGCCTTACCCAGAGAGACTCCTTCCACCTGGACGAG                        780

240
Gln Phe Thr Val Pro Val Gln Met Met Gln Ala Arg Thr Tyr Pro Leu Arg Trp Phe Leu
CAGTTCACGGTGCCCGTGGAAATGATGCAGGCCCGCACGTACCCGCTGCGCTGGTTCTTG                        840

260
Leu Glu Gln Pro Glu Ile Gln Val Ala His Phe Pro Phe Lys Asn Asn Met Ser Phe Val
CTGGAGCAGCCTGAGATCCAGGTGGCTCATTTCCCCTTTAAGAACAACATGAGCTTTGTG                        900

280
Val Leu Val Pro Thr His Phe Glu Trp Asn Val Ser Gln Val Leu Ala Asn Leu Ser Trp
GTCCTTGTACCCACCCACTTTGAATGGAACGTGTCCCAGGTACTGGCCAACCTGAGTTGG                        960

300
Asp Thr Leu His Pro Pro Leu Val Trp Glu Arg Pro Thr Lys Val Arg Leu Pro Lys Leu
GACACCCTGCACCCACCTCTGGTGTGGGAGAGGCCCACCAAGGTCCGGCTGCCTAAGCTG                       1020

320
Tyr Leu Lys His Gln Met Asp Leu Val Ala Thr Leu Ser Gln Leu Gly Leu Gln Glu Leu
TATCTGAAACACCAAATGGACCTGGTGGCCACCCTCAGCCAGCTGGGCCTGCAGGAGTTG                       1080

340
Phe Gln Ala Pro Asp Leu Arg Gly Ile Ser Glu Gln Ser Leu Val Val Ser Gly Val Gln
TTCCAGGCCCCAGACCTGCGTGGGATCTCCGAGCAGAGCCTGGTGGTGTCCGGCGTGCAG                       1140

360
His Gln Ser Thr Leu Glu Leu Ser Glu Val Gly Val Glu Ala Ala Ala Ala Thr Ser Ile
CATCAGTCCACCCTGGAGCTCAGCGAGGTCGGCGTGGAGGCGGCGGCGGCCACCAGCATT                       1200

380
Ala Met Ser Arg Met Ser Leu Ser Ser Phe Ser Val Asn Arg Pro Phe Leu Phe Phe Ile
GCCATGTCCCGCATGTCCCTGTCCTCCTTCAGCGTGAACCGCCCCTTCCTCTTCTTCATC                       1260

400
Phe Glu Asp Thr Thr Gly Leu Pro Leu Phe Val Gly Ser Val Arg Asn Pro Asn Pro Ser
TTCGAGGACACCACAGGCCTTCCCCTCTTCGTGGGCAGCGTGAGGAACCCCAACCCCAGT                       1320
```

-continued

```
                                                     420
Ala Pro Arg Glu Leu Lys Glu Gln Gln Asp Ser Pro Gly Asn Lys Asp Phe Leu Gln Ser
GCACCGCGGGAGCTCAAGGAACAGCAGGATTCCCCGGGCAACAAGGACTTCCTCCAGAGC          1380

440
Leu Lys Gly Phe Pro Arg Gly Asp Lys Leu Phe Gly Pro Asp Leu Lys Leu Val Pro Pro
CTGAAAGGCTTCCCCCGCGGAGACAAGCTTTTCGGCCCTGACTTAAAACTTGTGCCCCCC          1440

452
Met Glu Glu Asp Tyr Pro Gln Phe Gly Ser Pro Lys
ATGGAGGAGGATTACCCCCAGTTTGGCAGCCCCAAG                                  1476
```

3. cDNA encoding a leader amino acid sequence which consists of the following amino acid sequence:

```
   -39                                                                -21
   Met Ala Leu Leu Trp Gly Leu Leu Val Leu Ser Trp Ser Cys Leu Gln Gly Pro Cys
   ATGGCGCTGCTCTGGGGGCTCCTGGTGCTCAGCTGGTCCTGCCTGCAAGGCCCCTGC          60

-20                                                                 -1
   Ser Val Phe Ser Pro Val Ser Ala Met Glu Pro Leu Gly Arg Gln Leu Thr Ser Gly Pro
   TCCGTGGGCTCCCCTGTGAGCGCCATGGAGCCCTTGGGCCGGCAGCTAACTAGCGGGCCG       120
```

4. cDNA of claim 3 which consists of the following base sequence:

```
   -39                                                                -21
   Met Ala Leu Leu Trp Gly Leu Leu Val Leu Ser Trp Ser Cys Leu Gln Gly Pro Cys
   ATGGCGCTGCTCTGGGGGCTCCTGGTGCTCAGCTGGTCCTGCCTGCAAGGCCCCTGC          60

-20                                                                 -1
   Ser Val Phe Ser Pro Val Ser Ala Met Glu Pro Leu Gly Arg Gln Leu Thr Ser Gly Pro
   TCCGTGGGCTCCCCTGTGAGCGCCATGGAGCCCTTGGGCCGGCAGCTAACTAGCGGGCCG       120
```

5. Genomic DNA encoding a human α$_2$-plasmin inhibitor protein consisting of exons II, III, IV, V, VI, VII, VIII, IX and X having base sequences as shown below, said exons being connected to one another via introns which have base sequences or sizes as shown below, a first portion of said genomic DNA consisting of from exons II to VII and being contained in the base sequence of pUC19 plasmid, pPI62 bearing ATCC Designation No. 75142, and a second portion of said genomic DNA consisting of from exons VII to X and being contained in the base sequence of charon 4A phage, lambda PI2 bearing ATCC Designation No. 75143:

```
                                                    -1 +1
                                                  G AAC ATG GCG CTG CTC       ⎤
                                                         Met Ala Leu Leu      ⎬ EXON II
                                                          10                  ⎦

20              30              40              50              60
TGG GGG CTG GTG CTC AGC TGG TCC TGC CTG CAA GGC CCC TGC TCC GTG GTG AGC TGG TGA AGT GCA AGT GGG TGG GTG AGG GGA AGA GGG
Trp Gly Leu Val Leu Ser Trp Ser Cys Leu Gln Gly Pro Cys Ser Val
               -30                         -20

⎤
                70              80                                                                                     ⎬ EXON III
CTT GGC ATG AGG AGG GCT TGG CTC CGA GGG GAC CTC CTA TCC TCA TCC CTT TCT CCA CAG TTC TCC CCT GTG AGC GCC ATG GAG CCC TTG GGC CGG ⎦
                                                 Phe Ser Pro Val Ser Ala Met Glu Pro Leu Gly Arg
                                                  intron 2                 -10

90
CTT GGC ATG AGG AGG GCT TGG CTC CGA GGG GAC CTC CTA TCC TCA TCC CTT TCT CCA CAG TTC TCC CCT GTG AGC GCC ATG GAG CCC TTG GGC CGG
        GGG GCT GGG AGT GAG GAG CCT GTG ATG GGG GGA AGG TCC CGG GGA AGG TCC CAC TGG CCT TGG GCA GGG GCC TGT GGG AAG GGT CGG
 100                                                                      intron 3
 ─
 CAG
 Gln 110             120                130             140              150             160                        ⎤
 TCT CCA TCT GCT TGC TCC TTT CCG CAG CTA ACT AGC GGG CCG AAC CAG GAG CAG GTG TCC CCA CTT ACC CTC AAG TTG GGC AAC CAG GTA CAA     ⎬ EXON IV
                          Leu Thr Ser Gly Pro Asn Gln Glu Gln Val Ser Pro Leu Thr Leu Lys Leu Gly Asn Gln                         ⎦
                           -1 +1                                    10

170             180             190             200             210             220             230              240
CCA GGT GGG GCT GGG GAA GAG TGG GCG GGA GGG GTA GAG GGG GAG GGT GGG GCG GGA GGA CGA GAG AAG GGA AGG GCC GTG CCA ATG GGG CCC CTG TGC AGC AGA AGT CCC CCA GGA GTC TGC AGC AGA GAC ACC CCA GAG CAG ACC CAC AGG
                                                                 intron 4                                           Glu Pro Gly Gly Val Cys Ser Arg Asp Thr Pro Glu Gln Thr His Arg
                                                                                                                                                                          40

GAG TCC AGA GGC CAG AAG AGA GGA AAG GGA AGG CCT GTT CCT CAG GCA CAG GGG CTG TGA CAA GGC CTT CAA GAC CTG AGC TG  AC  CCC TTG ACC TCC CTG ACC
GGG GCT GGG ACA AGG CCC TGT CCT CAG GCA CAG GGG CTG TGA CAA GGC CTT CAA GAC CTG AGC TG  AC 250             260             270             280             290             300             310             320                      ⎤
CCT GAT CTG TCC CTG CAG GAG CCT GGT GGG CAG ACT GCC GAC TTC ACT GCC TTC CTG TTC CTG GTG GCT CTG GTT TCC CTG GTG GCT CTG TCA CCC CTG ATC TCA        ⎬ EX-
Leu Asp Leu Ser Leu Gln Glu Pro Gly Gly Gln Thr Ala Asp Phe Thr Ala Leu Phe Leu Val Ala Leu Val Ser Leu Val Ala Leu Ser Pro Leu Ile Ser            ⎬ ON
                                                                                                                      70                             ⎦ V

330
CTG GCC CGG GCC ATG ATG GCC TTC ATG GCA CTA GGT ATC CCA TGG TCC TAT CCT ATC TCT AGT CCA GCA CCA AGA GAG CTG GGA GGC C
Leu Ala Arg Ala Met Met Ala Phe Met Ala Leu Gly 340     350     360
GCC CTG GCG CTG TCT CAC CTG GCA CTG CTG GCA CTG
Ala Leu Ala Leu Ser His Leu Ala Leu Leu Ala Leu intron 5 (~1.5 kb)

370                                                    ⎤
..................................................................................... C CGG CCT CAG CCT TCG GTG CCT CCA GGT GCT CAG                ⎬ EX-
                                                                                                         ly Ala Gln                                         ⎦ ON V
```

```
                                                                                                    EXON VI
      380           390          400          410          420          430          440          450          460          470
AAC CAC ACG TTG CAG AGG CTG CAA CAG GTG CTG CAC GCA GGC TCA GGG CCC TGC CTC CCC CAT CTG CTG AGC CGC CTG TGC CAG GAC CTG GGC CCC
Asn His Thr Leu Gln Arg Leu Gln Gln Val Leu His Ala Gly Ser Gly Pro Cys Leu Pro His Leu Leu Ser Arg Leu Cys Gln Asp Leu Gly Pro
                              100                                                                                    120

480           490          500          510
GGC GCG TTC CGA CTG GCT GCC AGG ATG TAC CTG CAG AAA GGT AGG CGC TGA TGG CAG GGA GCT CCC TCA GTC CTG CCC TGG GTG GAG GAG GGT GAG
Gly Ala Phe Arg Leu Ala Ala Arg Met Tyr Leu Gln Lys G
                              130 intron 6
AGC AAG GGG CTG GGC CTC TGG TAG CGA GTA GGG GCG TGT CTG GCT GTG GAG CCT GGA ACA GCT GTG CTG CCT CCC GTG CAG GA TTT
                                                                                                            ly Phe 520           530          540          550          560          570          580          590          600          610
CCC ATC AAA GAA GAT TTC CTG GAA CAA TCC GAA CAG CTA TTT GGG GCA AAG CCC GTG AGC CTG ACG GGA AAG CAG GAA GAT GAC CTG GCA AAC ATC
Pro Ile Lys Glu Asp Phe Leu Glu Gln Ser Glu Gln Leu Phe Gly Ala Lys Pro Val Ser Leu Thr Gly Lys Gln Glu Asp Asp Leu Ala Asn Ile
                              150                                                                                    170

620           630          640          650          660          670          680          690          700
AAC CAA TGG GTG AAG GAG GCC ACG GAG AAA ATT CAG GAA TTC CTC TCT GGG CTG CCG GAA GAC GTG TTG CTT CTC CTC AAC GCC ATC CAC
Asn Gln Trp Val Lys Glu Ala Thr Glu Lys Ile Gln Glu Phe Leu Ser Gly Leu Pro Glu Asp Val Leu Leu Leu Asn Ala Ile His
                              180                                                                                    190

710
TTC CAG GGT GCG CTC TCT CTT AGA TCC CCC ACC CTG TAG GCT GAG CTG GAC GTC CAG GCC TTT TTG TTT TTT GAG ACA GTC TCG CTC TGT CAC AGG
Phe Gln G
                                                                                                                    200

TGA GGA TGG TCT GGT CTC A......... intron 7(~0.7 kb)................ CCT CCT CTC CAA CTG TCC CTC GAC TCA CCC CTC CCT CTC TGG GTT TCA GGT
                                                                                                                                    ly 720           730          740          750          760          770          780          790          800          810
TTC TGG AGG AAC AAG TTT GAC CCG AGC CTT ACC CAG AGA GAC TTC CAC CAG GAG TTC ACG GTG CCC GTG GAA ATG ATG CAG GCC CGC
Phe Trp Arg Asn Lys Phe Asp Pro Ser Leu Thr Gln Arg Asp Phe His Gln Glu Phe Thr Val Pro Val Glu Met Met Gln Ala Arg
                              210                                                                                    230

820           830          840          850
ACG TAC CCG CTG CGC TGG TTC TTG CTG GAG CAG CCT GAG ATC CAG GAG GTT CTC G........       intron 8(~3.1 kb)........
Thr Tyr Pro Leu Arg Trp Phe Leu Leu Glu Gln Pro Glu Ile Gln Glu Val Leu
                              240

EXON VIII
................TC TAG ACA CTC TGC CAC CAC TAG ACC CAC TTT CCT CAT GCT CTT CCC TTC CCA TTT CTG TAG 860           870          880          890          900          910          920          930          940          950
GTG GCT CAT TTC CCC TTT AAG AAC AAC ATG AGC TTT GTG GTC CTT GTA CCC ACC CAC TTT GAA TGG TCC CAG GTA AAC CTG GCC AAC CTG AGT
Val Ala His Phe Pro Phe Lys Asn Asn Met Ser Phe Val Val Leu Val Pro Thr His Phe Glu Trp Asn Val Leu Ala Asn Leu Ser
                              250                                                                                    270
```

-continued

```
                                                                                                                        EXON
                                                                                                                        IX
      960         970         980         990        1000        1010        1020        1030        1040        1050
TGG GAC ACC CTG CAC CCA CCT CTG GTG TGG GAG AGG CCC ACC AAG GTC CGG CTG CCT AAG CTG TAT CTG AAA CAC CAA ATG GAC CTG GTG GCC ACC
Trp Asp Thr Leu His Pro Pro Leu Val Trp Glu Arg Pro Thr Lys Val Arg Leu Pro Lys Leu Tyr Leu Lys His Gln Met Asp Leu Val Ala Thr
 280                                        290                             300                             310
      1060
CTC AGC CAG CTG GGT AAG GAG GAG GCG GGC GAG CCC GAG GTC AGC TGG GCA AGG CGG GAA ............ A AGA CAC AGG ACT CAC CAG GCA GCT
Leu Ser Gln Leu G
                                                         intron 9 (~1.1 kb)

EX-
                                                                                                                        ON
                                                                                                                        X
     1070        1080        1090        1100        1110        1120        1130
CTG ACC ACC ATC TCT GCC CTG CAG GAG TTG CAG GCC CCA GAC CTG TTT GGG ATC TCC GAG CAG AGC CTG GTG GTG TCC GGC GTG
Leu Thr Thr Ile Ser Ala Leu Gln Glu Leu Gln Ala Pro Asp Leu Phe Gly Ile Ser Glu Gln Ser Leu Val Val Ser Gly Val
                             ly Leu Gln Glu Leu Gln Ala Pro Asp Leu Phe Gly Ile Ser Glu Gln Ser Leu Val Val Ser Gly Val
                                     320                             330
     1140        1150        1160        1170        1180        1190        1200        1210        1220        1230
CAG CAT CAG TCC ACC CTG GAG CTC AGC GAG GTG GGC GCG GCG GCA GCG GCC CTG GAC CTG ACC GCC AGC ATT GCC ATG TCC CGC ATG TCC CTG TCC TCC TTC AGC
Gln His Gln Ser Thr Leu Glu Leu Ser Glu Val Gly Ala Ala Ala Ala Ala Leu Asp Leu Thr Ala Ser Ile Ala Met Ser Arg Met Ser Leu Ser Ser Phe Ser
         340                             350                             360                             370
     1240        1250        1260        1270        1280        1290        1300        1310        1320
GTG AAC CGC CCC TTC TTC ATC GAG GAC CAG GAT TCC CCG GGC CTT CTC CAG AGC TTC GTG GGC AGC GTG AGG AAC CCC AGT GCA CCG CGG
Val Asn Arg Pro Phe Phe Ile Glu Asp Gln Asp Ser Pro Gly Leu Leu Gln Ser Phe Val Gly Ser Val Arg Asn Pro Ser Ala Pro Arg
         380                             390                             400
     1330        1340        1350        1360        1370        1380        1390        1400        1410        1420
GAG CTC AAG CAA CAG CAG ATG GAG GAG GAT TAC CCC CAG TTT GGC AGC CTG AAA GGC TTC CCC CGC GGA GAC AAG CTT TTC GGC CCT GAC TTA
Glu Leu Lys Gln Gln Gln Met Glu Glu Asp Tyr Pro Gln Phe Gly Ser Leu Lys Gly Phe Pro Arg Gly Asp Lys Leu Phe Gly Pro Asp Leu
                 410                             420                             430
     1430        1440        1450        1460        1470        1480        1490        1500        1510
AAA CTT GTG CCC CCC ATG GAG GAG GAT TAC CCC CAG TTT GGC AGC CTG AAA TGA GGG GCC GTG GCA TCC AGA GTC CCT GCC TGG ACC AGC
Lys Leu Val Pro Pro Met
         440                             450
CTC TCC ACT CAT GTG ACT CTT TCC AAC CTG CTT TGT GGA GGA GGG GCG CGG CTG GAA GGG AGG GCA TCG GGG AGC CGG GAG CCT GAC CCT CAT CTT TCT TCC CAA CAC CTC TTG
GGG AGT TTA GGG TGG GGG GCG GGC GCC TGG GCA GGA GGG AGG TGC TTC TAG TTC TGC CAG GAG ACA GGT TAG CTG GAC ACA CCC GAC TT CAG AGG
GTG TCC TGC ACC GGG GCC TGG GCA GGA AGG GGG AGA GGG CTG CCT TTG GAC TTG TCC CGG GAC ACC TAG GCT AGG GTG GGG AGA GAC GGG CCC TGG TGG
TTG TTT ACC AGA GAA AAA GGG AGG GGG AGA GGC GTT GTC CTC AGC CCC GCG TGG AAC TCG TGT CTG GCA CAG CCT GGC TGT GGC CTA ACC TGC CGA GAG TCC ATC AGC CTC CAT
CTC GGG AGG CGA AGC GTT GTC CTC AGC CCC GCG TGG AAC TCG TGT CTG GCA CAG CCT GGC TGT GGC CTA ACC TGC CGA GAG TCC ATC AGC CTC CAT
```

```
CCT ACC CCC TGT GCC TTG TCA CGC CAG ACT TCC CAC GGC TCC CAG CAT TTC CCT CCT CCT
CAA CAC TGC CAG CAT TTC CTC TCC TGT CTC CCT CCT
CTG CCC GGG AGC TCA GGA ACC GAG GCA GGG AAG GAT CCC ATG AGC TCC TTA AGG CTC TTT TGT AAG GTT TTT
GTA GTG ATT TTT ATG CCA CCT GAA
TAA AGA ATG AAT GGG CGC TGT GGT TTT TTG CAC CGT TCT CGC 2232
```

6. The genomic DNA of claim 5 consisting of the following base sequence, wherein exon I having the following base sequence is linked upstream of exon II via intron I having a size of about 8kb, the first portion of said genomic DNA consisting of from exons I to VII and being contained in the base sequence of pUC19 plasmid, pPI62 bearing ATCC Designation No. 75142, and the second portion of said genomic DNA consisting of from exons VII to X and being contained in the base sequence of charon 4A phage, lambda PI2 bearing ATCC Designation No. 75143:

```
CCT TGG GAG CCA GTT GCA CTG CAG............
..........intron 1 (~8 kb)............                                                                    ⎫
                                                                                                          ⎪
                                      -20          -10                                                    ⎪ EXON I
                                      ACT AAC TGG GCA GGG AGG TAG CCT CTC GGT CCA                         ⎭

AAA AAT CCC AAA AGA CGG
TCT TAT TTG GTC CTC ACC ATG CAT GTG AGA AGA GTG AGG GAC TTT GTG CCA CCG TTT TAC AAG GTA AGG CCA AGC CTG GAG TTA CGG GTG GAG ATG
CCA GGT CCT TTG GCA AGA GGT AGC CTG GAT TCA GAC ACA GAT CTG ATT CAC AGC GCA GGG CCT TGT AGA ATG AGC ACG TTT TTG ATT TGG TAT CTC
CCT CCT ATT CAC CAA AAC ACC CTC AGT GCA TGA AAT GCA TGA AAT ATG AAA CAC CAG AAA CTA AAA AGG GGG AGA AGC CTG GGC AGA TGT CCC AGC
TGC AGG AGT GGG AGC CGC TGC TCG TGT GTT TGG GGT CTC TTC TGA GCC TTC TGA TTC CCC TTG GCA ATC ATG GCC TTT GCA GCC CCA GGA CTT GGC GTT
                                                                                                   ⎫
                                                                      -1 +1                        ⎪ EXON
ATC TGT GAT CGC GTG GGT AGG ATT CCT GGC GGG CGT GGG GAT GTG CAG ATG GGA ACA GAG CTT TCT GTC CCT GCC ⎬ II
                                                                      Met Ala Leu Leu              ⎪
                                                                         10                        ⎭
                                                                                                   ⎫
               20                30                40                50                60          ⎪
CAC AGG AAC ATG GCG CTG CTG CTC GTG CTC CTG GTG CTC AGC TGG TCC TGC CTG CAA GGC CCC TGC TCC GTG    ⎪
Trp Gly Leu Leu Val Leu Ser Trp Ser Cys Leu Gln Gly Pro Cys Ser Val                                ⎪ EX-
-30                                                       -20                                      ⎬ ON
                                                                                                   ⎪ III
               70                80                90                                              ⎪
CTT GGC ATG AGG AGG GCT TGG CTC CGA GGG GAC CTC CTA TCC TCA CCC CTT TCT CCA CAG TTC TCC CCT GTG AGC GCC ATG GAG CCC TTG GGC CGG ⎭
                                                                   Phe Ser Pro Val Ser Ala Met Glu Pro Leu Gly Arg
                                                                                                       -10
intron 2                                          intron 3
               100
CAG GTA CTG GGG AGT GAG GAG CCT GTG ATG GGG GTG CCC CGC CAG GGG AGG TCC CGG GGG TCT CAC TGG TGG CCT TGG GCA GGG TGG GGG GCC TGT GGG AAG GGT CGG
Gln
                                                                                                                                                ⎫
              110                 120                 130                 140                 150                 160                           ⎪
TCT CCA TCT GCT TGC TCC TTT CCG CAG CTA ACT AGC GGG CCG AAC CAG GAG CAG CAG GTG TCC CCA CTT ACC CTC AAG TTG GGC AAC CAG GTA CAA                 ⎬ EXON IV
                Leu Thr Ser Gly Pro Asn Gln Glu Gln Gln Val Ser Pro Leu Thr Leu Lys Leu Gly Asn Gln                                             ⎪
                    -1 +1                                                          10                                                           ⎭
intron 4
CCA GGT GGG GCT GGG GAA GAG TGG GCG GGG CTA GAG GGA GGA GGG CCC ATC GGC AGG GGT CGG GGG GTG GGG GCG CCC AGA ATG CCA GGC CCC TCC GTC TGA CGC TCC CTG GAG GCT CTG
GAG TCC AGA GAG GCC CAG AAG GGA AAG GGT CGG GGA GAG GAC CGA GGG GAG GAC GCG CCA AGG TGG GCG AGA GTG CCC AGA ATG CCA GGC CCC TCC GTC TGA CGC TCC CTC TTC CCT
```

-continued

```
GGG GCT GGG ACA AGG CCC TGC TGT CCT CAG GCA CAG GGG CTG TGA CAA GGC CTT CAA CAC AGA ACC TGG AGC TG      AC    CCC TTG ACC TCC CTG ACC
     170              180              190              200              210              220              230              240

CCT GAT CTG TCC CTG CAG GAG CCT GGT GGC CTG AGT GCC CTG AAG AGT CCC CCA GGA GTC AGC AGA GAC ACC CCA GAG CAG ACC CAC AGG                        ┐
Glu Ala Gly Gly Gly Gln Thr Ala Leu Lys Ser Pro Pro Gly Val Cys Ser Arg Asp Thr Pro Glu Gln Thr His Arg                                         │ EX-
                20                                  30                                  40                                                      │ ON
CTG GCC CGG GCC ATG ATG GCC TTC ACT GCC GAC TCC TTC CTG GTG GCT CAA ACG TCC ACC TGC ATC CTG TCA CCC CTG AGT GTG                                 │ V
Leu Ala Arg Ala Met Met Ala Phe Thr Ala Asp Ser Phe Leu Val Ala Gln Thr Ser Thr Cys Ile Leu Ser Pro Leu Ser Val                                 │
                50                                  60                                  70                                                      ┘
     250              260              270              280              290              300              310              320              330

GCC CTG GCG CTG TCT CAC CTG GCA CTA GGT ATC CCA GCA CTA GGT CCT TAT CCT AGT CCA AGA GAG CTG GGA GGC ............
Ala Leu Ala Leu Ser His Leu Ala Leu G
                80
     340              350              360

............ intron 5 (~1.5 kb) ............ C CGG CCT CAG CCT TCG GTG CCT CCA GGT GCT CAG   ┐
                                                                                  ly Ala Gln  │
                                                                                       470    │ EX-
                                                                                              │ ON
AAC CAC ACG TTG CAG AGG CTG CAA CAG GTG CTG CAC GCA GGG CCC TGC CTC CCC CAT CTG AGC CTC TGC CTC CTG AGC CGC CTC TGC CAG GAC CTG GGC CCC           │ VI
Asn His Thr Leu Gln Arg Leu Gln Gln Val Leu His Ala Gly Pro Cys Leu Pro His Leu Ser Leu Cys Leu Leu Ser Arg Leu Cys Gln Asp Leu Gly Pro          │
                90                                  100                                 110                                                      │
     380              390              400              410              420              430              440              450              460  │
                                                                                                                                                  │
GGC GCG TTC CGA CTG GCT GCC AGG ATG TAC CTG CAG AAA GGT AGG CGC TGA TGG CAG GGA GCT CCC TCA GTC CTG CCC TGG GTG GAG GAG GGT GAG                   │
Gly Ala Phe Arg Leu Ala Ala Arg Met Tyr Leu Gln Lys G                                                                                            │
                120                                 130                                                                                          ┘
     480              490              500              510
                                             intron 6
AGC AAG GGG CTG GGC CTC TGG TAG CGA GTA GGG GCG CTG GAG CCT GTG GAG CCT GTG CTG GCT GGA ACA GCT TGT GCT GCC TCC GTG CAG   GA TTT   ┐
                                                                                                                           ly Phe  │ EX-
                                                                                                                              610  │ ON
                                                                                                                                   │ VII
CCC ATC AAA GAA GAT TTC CTG GAA CAA CAA TCC GAA CAG CTA TTT GGG GCA AAG CCC GTG AGC CTG ACG GGA AAG CAG GAA GAT GAC CTG GCA AAC ATC │
Pro Ile Lys Glu Asp Phe Leu Glu Gln Gln Ser Glu Gln Leu Phe Gly Ala Lys Pro Val Ser Leu Thr Gly Lys Gln Glu Asp Asp Leu Ala Asn Ile │
                140                                 150                                                 160                          │
     530              540              550              560              570              580              590              600      │

AAC CAA TGG GTG GAG AAG GCC ACG GAG GAG AAG ATT CAG GAA TTC CTC TCT GGG CTG CCG GAA GAC ACC GTG TTG CTT CTC CTC AAC GCC ATC CAC      │
Asn Gln Trp Val Glu Lys Ala Thr Glu Glu Lys Ile Gln Glu Phe Leu Ser Gly Leu Pro Glu Asp Thr Val Leu Leu Leu Asn Ala Ile His          │
                170                                 180                                                 190                          ┘
     620              630              640              650              660              670              680              690       700
```

-continued

```
710
TTC CAG GGT GCG CTC TCT CTT AGA TCC CCC ACC CTG TAG GCT GAG CTG GAC GTG CAG GCC TTT TTG TTT TTT GAG ACA GTC TCG CTC TGT CAC AGG
Phe Gln Gly
     G

TGA GGA TGG TCT GGT CTC A......... intron 7(~0.7 kb)......... CCT CCT CTC CAA CTG TCC CTC GAC TCA CCC CTC CCT CTC TGG GTT TCA GGT
                                                                                                                              ly
                                                                                                                              200
720          730          740          750          760          770          780          790          800          810
TTC TGG AGG AAC AAG TTT GAC CCG AGC CTT ACC CAG AGA GAC TCC TTC CAC CTG GAC CTG TAG TCC TTC ACG CAG TTC ACG GTG CCC GTG GAA ATG CAG GCC CGC
Phe Trp Arg Asn Lys Phe Asp Pro Ser Leu Thr Gln Arg Asp Ser Phe His Leu Asp Leu   Ser Phe Thr Gln Phe Thr Val Pro Val Glu Met Gln Ala Arg
            210                              220                                                            230
820          830          840          850
ACG TAC CCG CTG CGC TGG TTC TTG CTG GAG CAG CCT GAG ATC CAG GTC ACC TTG TCT CCA GAG GTT CTC G......... intron 8(~3.1 kb)
Thr Tyr Pro Leu Arg Trp Phe Leu Leu Glu Gln Pro Glu Ile Gln
                240

........ TC TAG ACA CTC TGC CAC CAC TAG CTC GGC TTC TGT CCT CAT GCT CTT CCC TTC CCA TTT CTG TAG
860          870          880          890          900          910          920          930          940          950
GTG GCT CAT TTC CCC TTT AAG CCC TTT GTG GTC CTT GTA CCC CAC TTT GAA TGG AAC GTG TCC CAG GTA CTG GCC AAC CTG AGT
Val .Ala His Phe Pro Phe Lys Pro Phe Val Val Leu Val Pro Thr His Phe Glu Trp Asn Val Ser Gln Val Leu Ala Asn Leu Ser
       250                              260                                                            270
960          970          980          990          1000         1010         1020         1030         1040         1050
TGG GAC ACC CTG CAC CCA CCT CTG GTG TGG GAG AGG CCC ACC AAG GTC CGG CTG CCT AAG CTG TAT CTG AAA CAC CAA ATG GAC CTG GTG GCC ACC
Trp Asp Thr Leu His Pro Pro Leu Val Trp Glu Arg Pro Thr Lys Val Arg Leu Pro Lys leu Tyr Leu Lys His Gln Met Asp Leu Val Ala Thr
280                              290                                          300                                          310
1060
CTC AGC CAG CTG GGT AAG GAG GAG GGA GCG GGC GAG CCC GAG GTC AGC TGG GCA AGG CGG GAA......... intron 9(~1.1 kb)
Leu Ser Gln Leu G
           320

A AGA CAC AGG ACT CAC CAG GCA GCT
1070         1080         1090         1100         1110         1120         1130
CTG ACC ACC ATC TCT GCC CTG GCA GGG CTG CAG GAG TTG CAG GCC CCA GAC CTG CGT GGG ATC TCC GAG CAG AGC CTG GTG GTG TCC GGC GTG
ly  Leu Gln Glu Leu Phe Gln Glu Leu Phe Gln Glu Leu Ala Pro Asp Leu Arg Gly Ile Ser Glu Gln Ser Leu Val Val Ser Gly Val
    320                              330                                          340
1140         1150         1160         1170         1180         1190         1200         1210         1220         1230
CAG CAT CAG TCC ACC CTG GAG CTC AGC GAG CTG GGC GAG GTG GCG GCG GCA ACC ATT GCC ATG TCC CGC ATG TCC TCC TTC AGC
Gln His Gln Ser Thr Leu Glu Leu Ser Glu Leu Gly Glu Val Ala Ala Ala Thr Ile Ala Met Ser Arg Met Ser Ser Phe Ser
340                              350                                          360                                  370
```

```
                1240            1250            1260            1270            1280            1290            1300            1310            1320
GTG AAC CGC CCC TTC CTC TTC ATC TTC GAG GAC ACC ACA GGC CTT CCC CTC GTG GGC AGC GTG AGG AAC CCC AGT GCA CCG CGG
Val Asn Arg Pro Phe Leu Phe Ile Phe Glu Asp Thr Thr Gly Leu Pro Leu Val Gly Ser Val Arg Asn Pro Ser Ala Pro Arg
                                        380                                         390                                         400
                1330            1340            1350            1360            1370            1380            1390            1400            1410            1420
GAG CTC AAG CAA CAG CAG GAT TCC CCG GGC AAC AAG GAC TTC CTC CAG AGC CTG AAA GGC TTG GGC TTC CCC CGC GGA GAC AAG CTT GGC CCT GAC TTA
Glu Leu Lys Gln Gln Gln Asp Ser Pro Gly Asn Lys Asp Phe Leu Gln Ser Leu Lys Gly Leu Gly Phe Pro Arg Gly Asp Lys Leu Gly Pro Asp Leu
            410                                         420                                         430
        1430            1440            1450            1460            1470            1480            1490            1500            1510
AAA CTT GTG CCC CCC ATG GAG GAG GAT TAC CCC CAG TTT GGC AGC AGC CCC AAG TGA GGG GCT GTG GCA TCC AGA GTC CCT GCC TGG ACC AGC
Lys Leu Val Pro Pro Met Glu Glu Asp Tyr Pro Gln Phe Gly Ser Ser Pro Lys
        440                                         450

CTC TCC ACT CAT GTG ACT CTT TCC AAC CTG CTT TGT GGC ACT GGG GCA GGG CAG GCA TCG GGG GGC CGG GAG CCT GAC CTG CTC CCC ACG TCA GCT GGG ACA CCC GGA CTT

GGG AGT TTA GGG TGG GGG GCG GCG GCG CTG GGA GGA GGG AGG TGC TTC TAG TGC CAG GAG ACA GGT TAG CTG CTG CCT TGG GTA TAG CTG CTG CCT CAG AGG

GTG TCC TGC ACC GGG GCC TGG GCA GGA GGG AGG GGG AGA GGG CTG CCT TTG GAC TTG TCC CGG GAC ACC TAG GCT GGT AGG GRG GGG AGA GAC GGG CCC TGG TGG

TTG TTT ACC AGA GAA AAA GGG AGG GGG AGA AGC GTT GTC CTC AGC CCG TGG AAC TCG TGT CTG GCA CAG CCT GGC TGT GGC CTA ACC TGC CGA GAG TCC ATC AGC CTC CAT

CTC GGG AGG CGA AGC CCC TGT GCC TTG TCA CGC CAG ACT TCC CAC GGC TCC TCG AGA TCC CAA CAC TGC CAG CAT TTC CCT TCC TCC TTC CTC TCC TGT CTC CCT CCT

CCT ACC CCC GGG AGC TCA GGA ACC GAG GCA GGA AAG GAT CCC ATG AGC TCC TTA AGG CTC TTT TGT AAG GTT TTT GTA GTG ATT TTT ATG CCA CCT GAA

CTG CCC GGG AGC TCA GGA ACC GAG GCA GGA AAG GAT CCC ATG AGC TCC TTA AGG CTC TTT TGT AAG GTT TTT GTA GTG ATT TTT ATG CCA CCT GAA

TAA AGA ATG AAT GGG CGC TGT GGT TTT TTG CAC CGT TCT CGC 2232
```

7. Genomic DNA encoding a leader amino acid sequence which consists of exon II, intron 2, exon III, intron 3 and exon IV having the following base sequences, said genomic DNA being contained in the base sequence of pUC19 plasmid, pPI62 bearing ATCC Designation No. 75142:

```
                                                                                          EXON II
                                                      -1 +1                            10
                                                    G AAC ATG GCG CTG CTC
                                                      Met Ala Leu Leu
       20                30              40              50              60
TGG GGG CTC CTG GTG CTC AGC TGG TCC CTG TGC CTG CAA GGC CCC TGC TGC GTG TCC GTG GTG AGC TGG TGA AGT GGG TGG GTG AGG GGA AGA AGG
Trp Gly Leu Leu Val Leu Ser Trp Ser Leu Cys Leu Gln Gly Pro Cys Ser Val
                      -30                                           -20

EXON III
                             intron 2                        intron 3                              70              80              90
CTT GGC ATG AGG AGG GCT TGG CTC CGA GGG GAC CTC CTA TCC CTT TCT CCA CAG TTC TCC CCT GTG AGC GCC ATG GAG CCC TTG GGC CGG
                                                                     Phe Ser Pro Val Ser Ala Met Glu Pro Leu Gly Arg
     100
CAG GTA CTG GGG AGT GAG GAG CCT GTG ATG GGG GGA AGG TCC CGG GGG TCT CAC TGG GCA GGG TGG CCT TGG GGG ATG GGG AAG GGT CGG
Gln EX-ON IV
         110             120             130             140             150             160
TCT CCA TCT GCT TGC TCC TTT CCG CAG CTA ACT AGC GGG CCG AAC CAG GAG CAG GTG TCC CCA CTT ACC CTC AAG TTG GGC AAC CAG
                      Leu Thr Ser Gly Pro Asn Gln Glu Gln Val Ser Pro Leu Thr Leu Lys Leu Gly Asn Gln
                              -1 +1                                                      10
```

* * * * *